United States Patent [19]

Nomoto et al.

[11] 4,440,171

[45] Apr. 3, 1984

[54] SUTURING INSTRUMENT AND A METHOD OF HOLDING A SHUTTLE

[75] Inventors: Reishi Nomoto; Masayoshi Takahashi, both of Kanagawa; Yoshikazu Ebata, Tokyo, all of Japan

[73] Assignee: Janome Sewing Machine Co., Ltd., Kyobashi, Japan

[21] Appl. No.: 344,781

[22] Filed: Feb. 1, 1982

[30] Foreign Application Priority Data

Apr. 13, 1981 [JP] Japan .................................. 56-54436

[51] Int. Cl.³ ............................................. A61B 17/04
[52] U.S. Cl. ............................. 128/335.5; 128/334 R
[58] Field of Search ............... 128/334 R, 334 C, 335, 128/335.5

[56] References Cited

U.S. PATENT DOCUMENTS

| | | | |
|---|---|---|---|
| 349,791 | 9/1886 | Gibboney, Jr. | 128/335.5 |
| 3,037,619 | 6/1962 | Stevans | 128/334 R |
| 3,570,497 | 3/1971 | Lemole | 128/335.5 |
| 3,985,138 | 10/1976 | Jarvik | 128/335.5 X |
| 4,235,238 | 11/1980 | Ogiu et al. | 128/335 X |

FOREIGN PATENT DOCUMENTS 861469  2/1941  France .................................. 28/334

*Primary Examiner*—Lee S. Cohen
*Assistant Examiner*—Angela D. Sykes
*Attorney, Agent, or Firm*—Michael J. Striker

[57] ABSTRACT

A surgical suturing instrument crosses and knots a suturing thread combining a shuttle and the other suturing thread passing through an eye of a curved needle in a lock stitching practice, for accomplishing smooth passage of passing the shuttle through a loop of the needle thread and exact combination of the shuttle thread and the needle thread without getting out the shuttle from a shuttle holder during the suturing operation so as to form sound suturing stitchings every time. The shuttle is accommodated between a shuttle holder and a shuttle claw. The shuttle is formed with a front end portion movable between a guide groove in the shuttle claw and a guide groove in the shuttle holder. The shuttle is further formed with a sharp end for catching a thread loop in the suturing operation.

5 Claims, 18 Drawing Figures

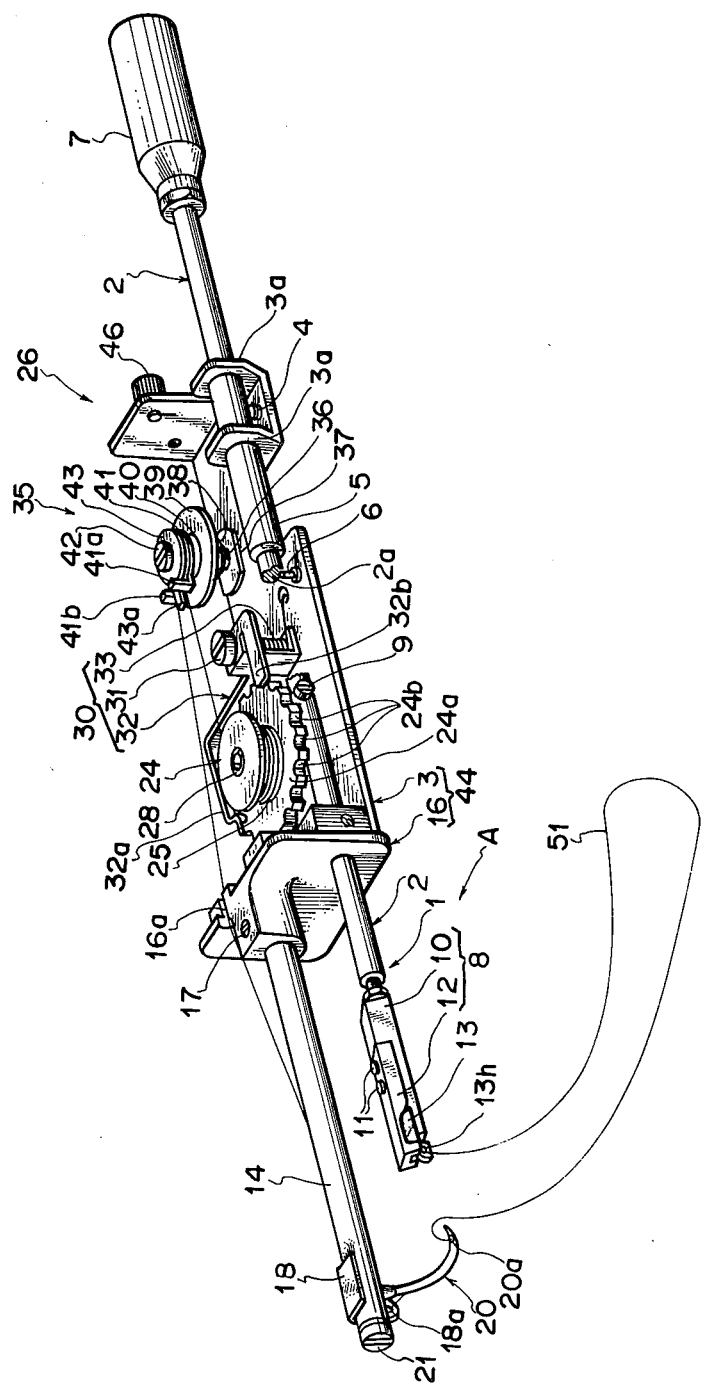
FIG_1

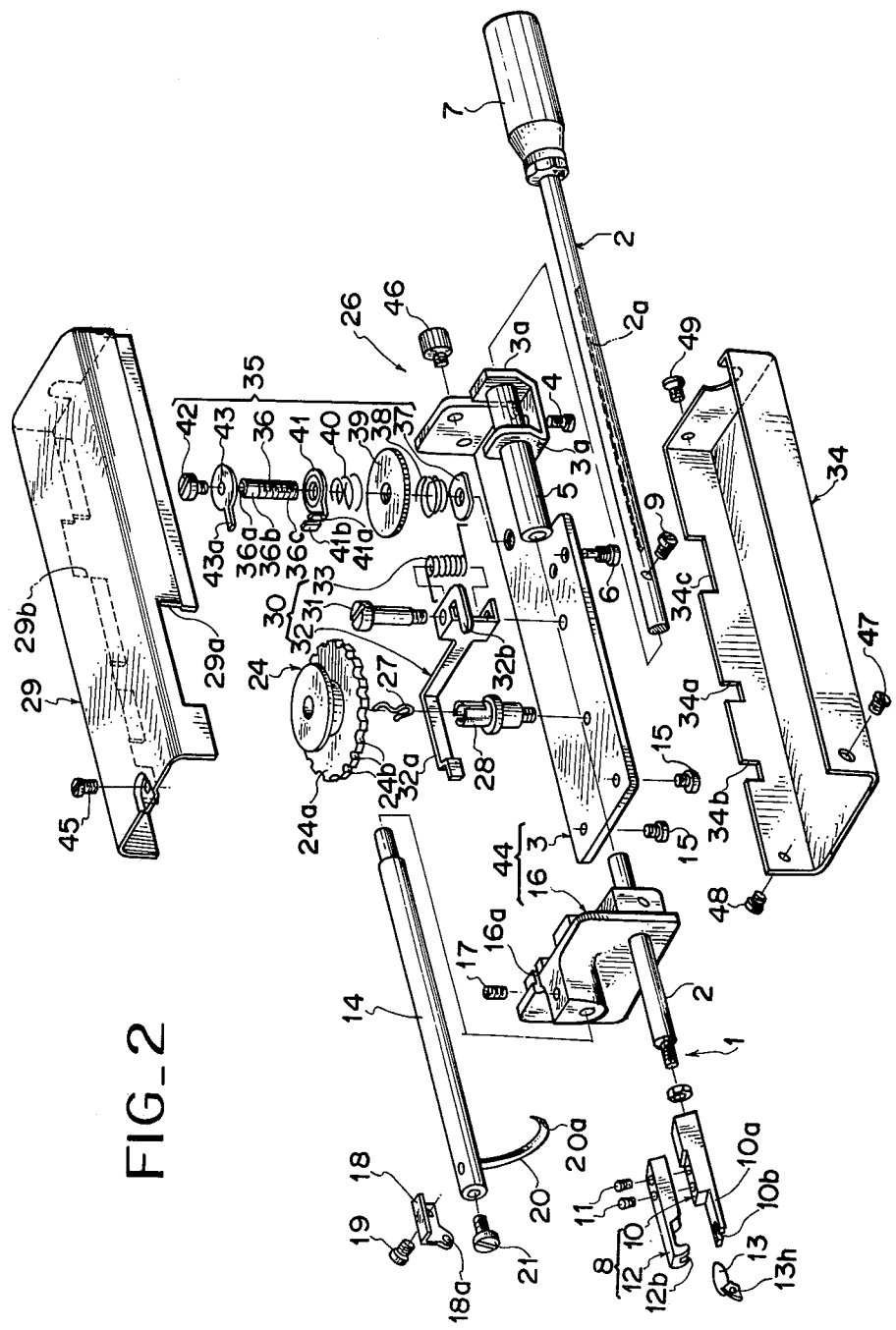
FIG_2

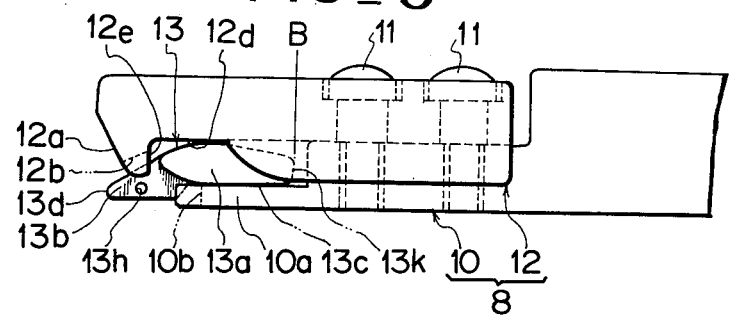
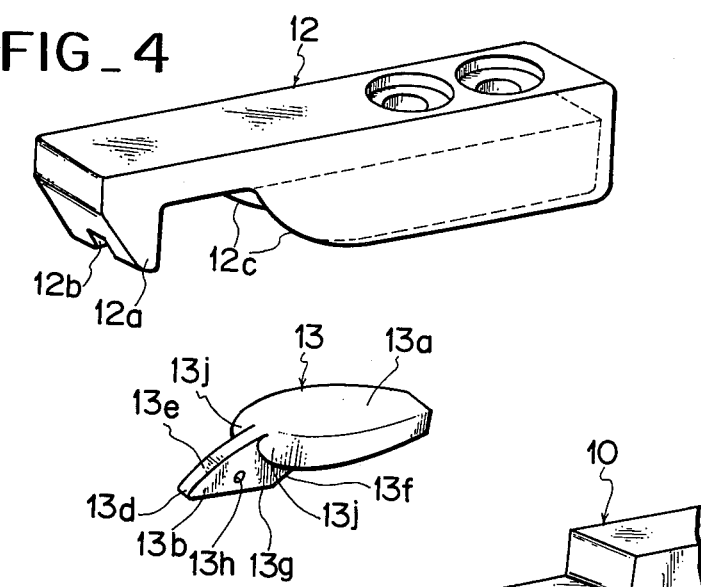
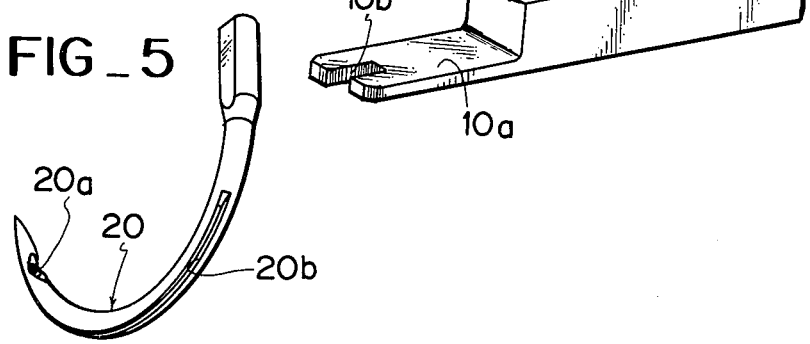

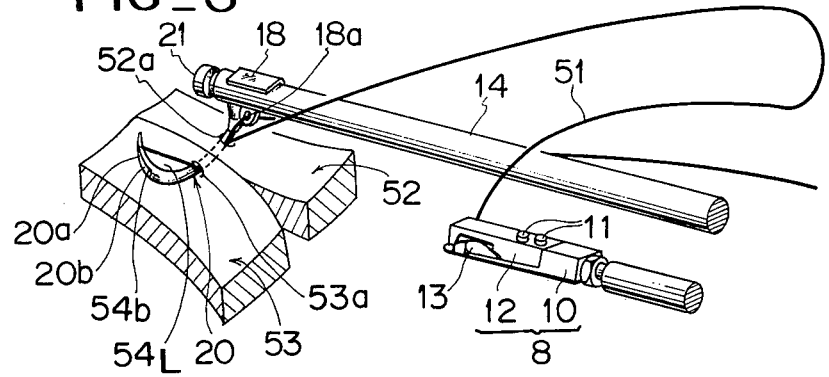
FIG_6
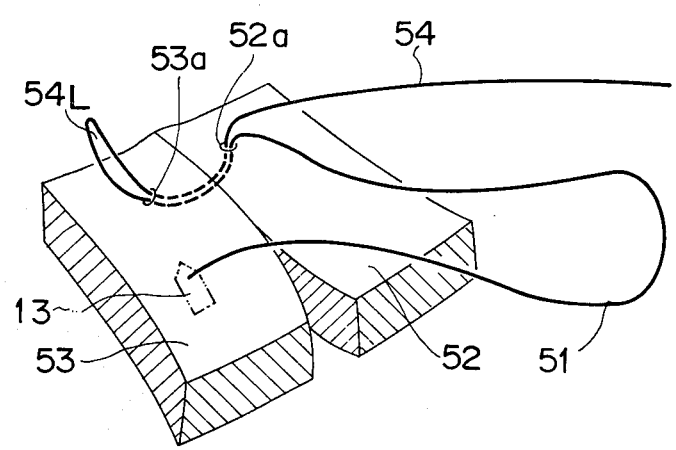
FIG_7
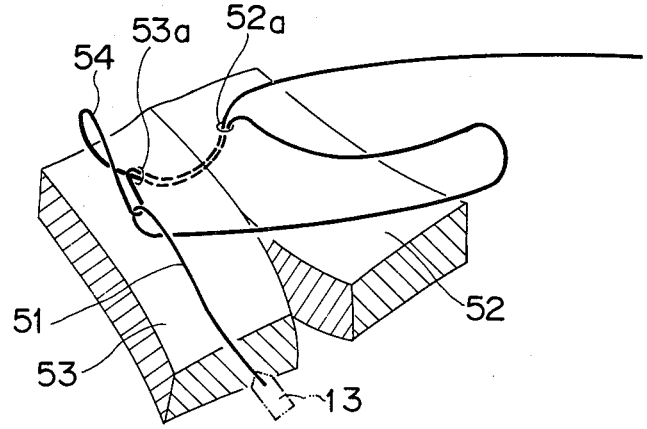
FIG_8

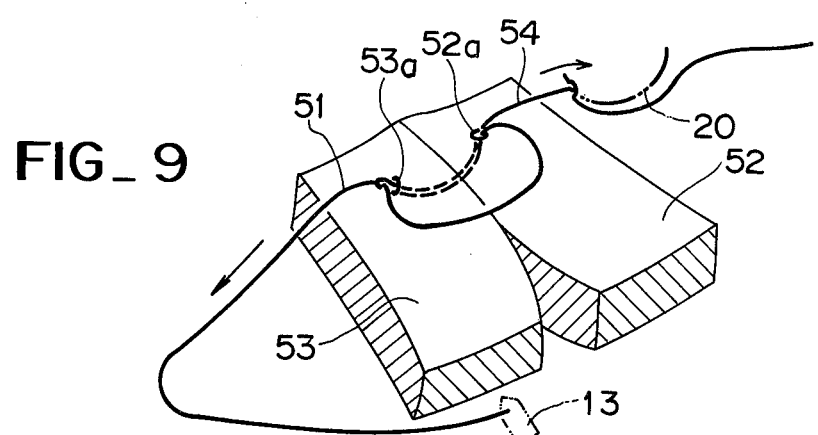
FIG_9
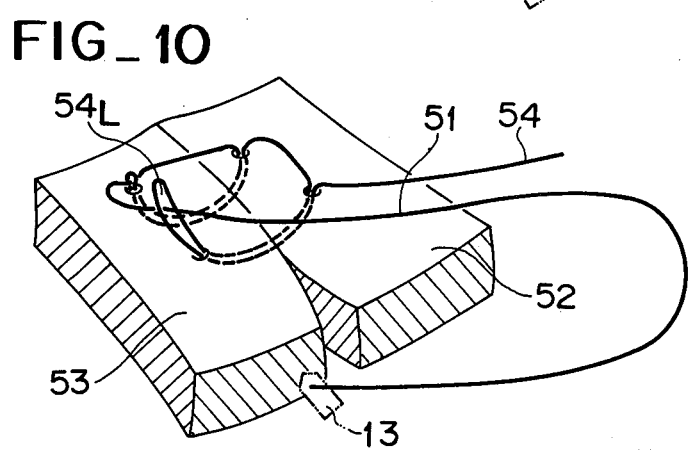
FIG_10
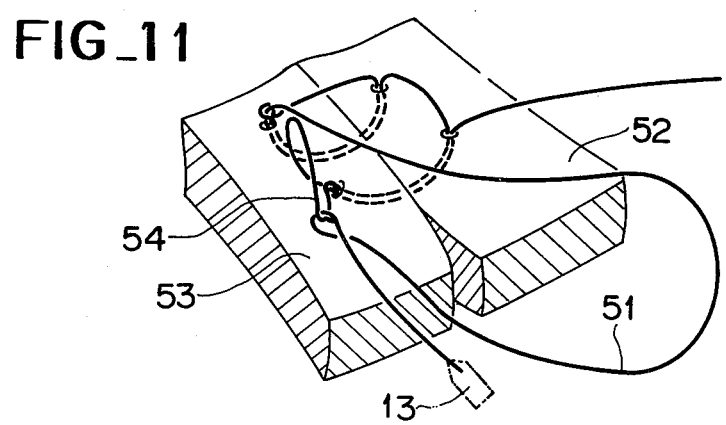
FIG_11

FIG_12
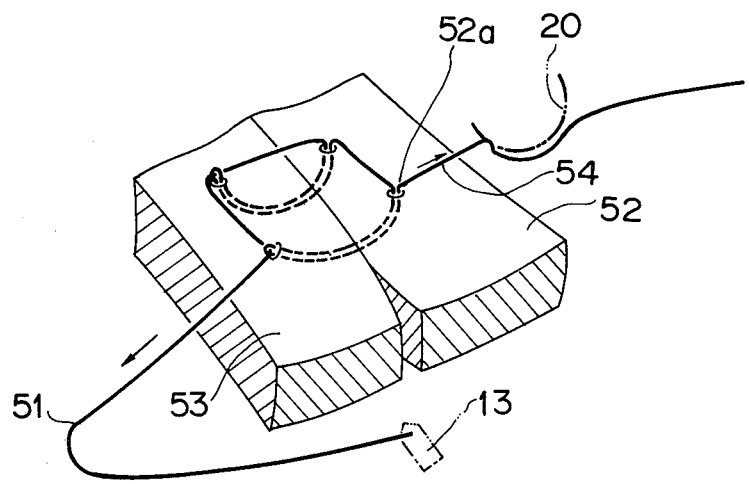
FIG_13
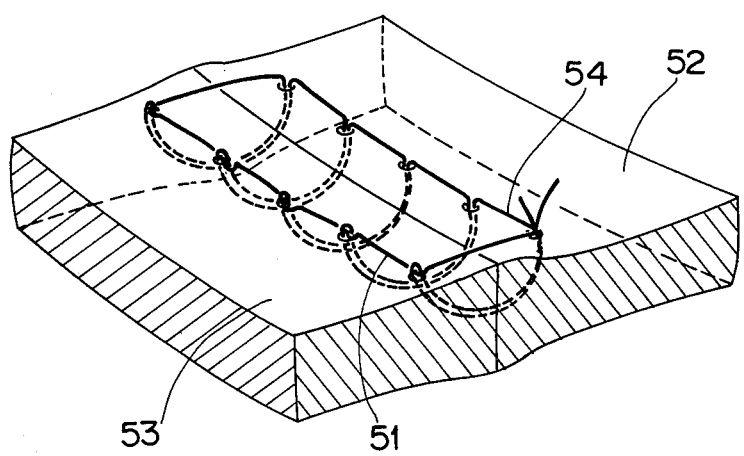

FIG_14
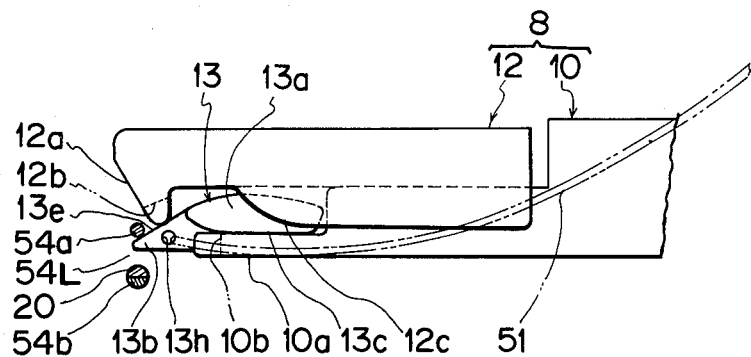
FIG_15
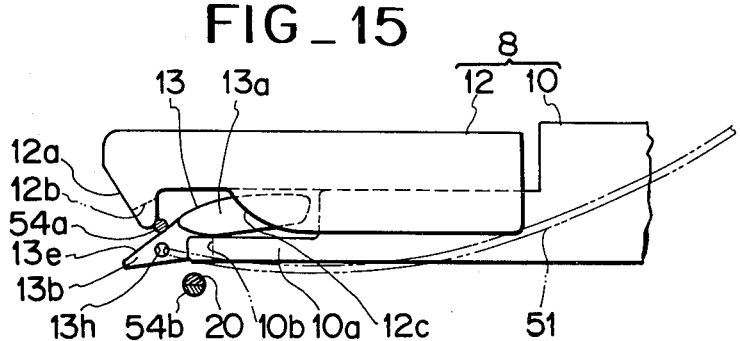
FIG_16
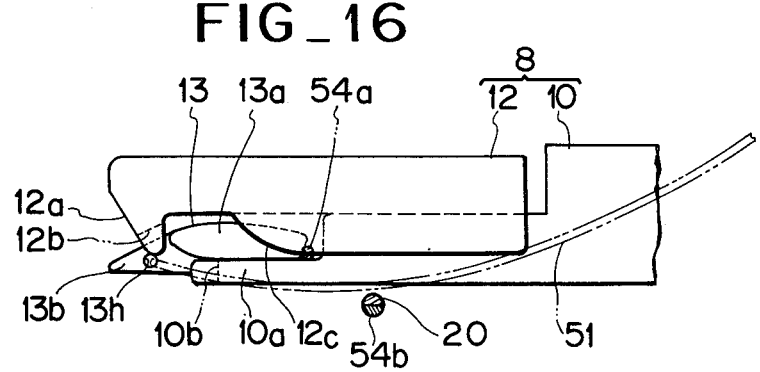

FIG_17
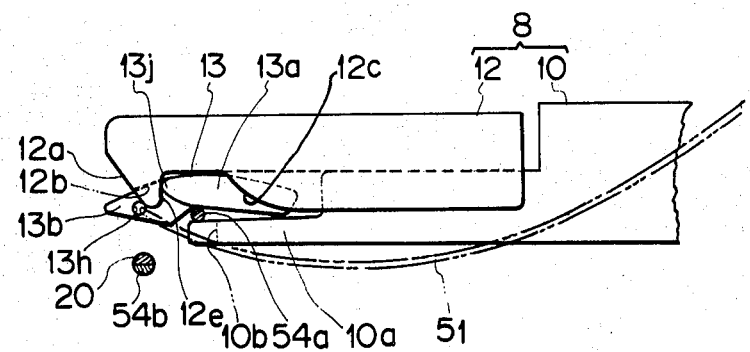
FIG_18
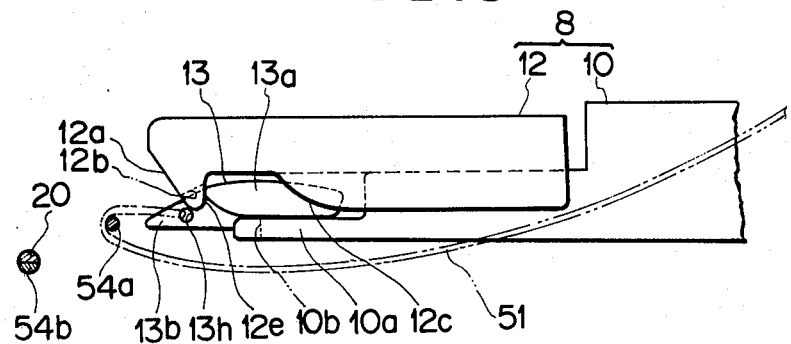

SUTURING INSTRUMENT AND A METHOD OF HOLDING A SHUTTLE

BACKGROUND OF THE INVENTION

The invention relates to a surgical suturing instrument and a method of holding a shuttle for a surgical operation for a human part to be sutured up by crossing a suturing thread combining to the shuttle and a suturing thread passing through an eye of a curved needle, in a lock stitching practice.

SUMMARY OF THE INVENTION

An object of the invention is the surgical suturing instrument which crosses and knots the suturing thread connected to the shuttle and the other suturing thread passing through the eye of the curved needle in the lock stitching, for accomplishing smooth passage of the shuttle through the loops of the needle thread and exact combination of the shuttle thread and the needle thread without getting out the shuttle from a shuttle holder during the suturing operation, so as to form sound stitchings every time.

BRIEF DESCRIPTION OF THE DRAWINGS

FIG. 1 is a perspective view of the suturing instrument, taking off a cover;

FIG. 2 is a perspective view of the disassembled suturing instrument;

FIG. 3 is a view seen from an arrow A of the shuttle holder in FIG. 1;

FIG. 4 is an exploded view of the shuttle holder;

FIG. 5 is a perspective view of a curved needle;

FIG. 6 is a perspective view showing the suturing condition of the suturing instrument;

FIGS. 7 to 12 are perspective views showing the suturing process after a first penetration of the curved needle in relation to the needle thread of which and the shuttle thread, FIG. 7 is a view showing relation between the needle thread and the shuttle thread in FIG. 6, FIG. 8 is a view showing a condition of crossing the shuttle thread into the loop of the needle thread, FIG. 9 is a view showing a condition of tightening the needle thread and the shuttle thread, FIG. 10 is a view showing a condition between the needle thread and the shuttle thread at second penetration of the curved needle, FIG. 11 is a view showing a condition of crossing the shuttle thread into the loop of the thread needle, and FIG. 12 is a view showing a condition of tightening the needle thread and the shuttle thread;

FIG. 13 is a perspective view showing a condition of completing the suturing operation; and FIGS. 14 to 18 are views showing processes of catching the loop of the needle thread by the shuttle, of which FIG. 14 is a view just after progressing of the shuttle into the loop of the needle thread, FIG. 15 and 16 show conditions of further progressing, FIG. 17 is a condition showing the shuttle holder going back with respect to the curved needle from the condition of FIG. 16, and FIG. 18 is a condition showing the needle thread loop getting out between the shuttle and the shuttle holder by successive retreat of the shuttle holder so that the needle thread and the shuttle thread are crossed each other.

DETAILED DESCRIPTION OF THE INVENTION

The present invention will be explained in reference to the embodiment thereof. In FIGS. 1 and 2, the numeral 1 is a shuttle holding member, a shaft of which passes through a couple of bendings 3a of a machine frame 3 and it slidably inserts into a pipe 5 secured to the machine frame by a screw 4. The shaft 2 is defined with a guide groove 2a which engages a rotation stopping pin 6 provided to the machine frame 3 of a suturing instrument generally denoted as 26, and it is provided with a handle 7 and a shuttle holder 8 at an opposite part thereto. By pushing operation of the handle 7, the shuttle holder 8 is reciprocating within determined range under a condition that it is restrained in rotation with respect to the machine frame 3. The numeral 9 is a stopping screw for restraining the reciprocation of the shuttle holding member 1.

The shuttle holder 8 is composed of a shuttle holder element 10 and a shuttle claw 12 secured to the shuttle holder element 10 by a screw 11, to hold a shuttle 13 therebetween.

Referring to FIGS. 3 and 4, the shuttle 13 is composed of a main body 13a and an end portion 13b extending therefrom, and is symmetrical with respect to a center line thereof. At the end portion 13b, there are provided a sharp end 13d for catching the needle thread loop, a slope 13e which smoothly connects the end 13d with the main body 13a, a slope 13f expanding downwardly from the bottom 13c of the main body 13a, and a connecting face 13g for connecting the slope 13f to the end 13d. The shuttle 13 is, as a whole, shaped in plate and is formed with a thread hole 13h for passing the shuttle thread.

The main body 13a is so shaped that it has lengthwise a continuous high portion along the center line in reference of the bottom 13c and it becomes lower in its width as being apart from the center line to the right and left. With respect to the vertical cross sectional shape in lengthwise direction, the main body 13a round at the front part and the height from the bottom 13c becomes lower in the rearward direction. The main body 13a is further so shaped that it becomes narrow in a couple of expanding round shoulders 13j in the rearward direction, and it is, as shown in FIG. 3, reduced in thickness with respect to a vertical part B at its rear end.

A tongue or a guide piece 10a of the shuttle holder element 10 is formed with a guide groove 10b for, if necessary, engaging and guiding the end portion 13b of the shuttle 13. A shuttle claw 12 is provided with a hook 12a which is formed with a guide groove 12b for, if necessary, engaging and guiding the end portion 13b of the shuttle 13, and it is further formed with a couple of shuttle guide pieces 12c at a rear part thereof.

Under condition that the shuttle 13 is supported by the shuttle holder 8, spaces are made respectively between an upper face of the main body 13a and an inner face of the shuttle claw 12, and the rear part of the main body 13a and the inner faces of the shuttle guide pieces 12c. The shuttle 13 goes into the needle thread loop as will be mentioned later and is effected with the external force via the needle thread loop and it is moved under condition that it is held by the shuttle claw 12 and the shuttle holder element 10 while the needle thread loop and the shuttle thread are crossing. In all the movable range, the end portion 13b of the shuttle 13 engages with at least one of the guide grooves 10b and 12b, and the shuttle smoothly gets out of the thread without slipping from the shuttle holder 8. The guide pieces 12c of the shuttle claw 12 serve to smoothly guide the needle thread loop from the upper surface of the shuttle main body 13a to the rear face 13k, (FIG. 3) when the shuttle 13 goes into the needle thread loop, as will be later mentioned.

Again referring to FIGS. 1 and 2, a needle bar 14 is fixed at its one end with a screw 17 to a needle bar supporter 16 which is secured to the machine frame 3 with screws 15, and is provided at its other end with a thread guide piece 18 by a screw 19 so that a curved needle 20 is detachably attached thereto with a screw 21. The curved needle 20 is, as shown in FIG. 5, formed with a needle hole 20a at its end, and is defined with an oblong groove 20b.

The numeral 24 (FIGS. 1 and 2) is a thread supply for coiling a suturing thread 25 thereon, which is provided on the machine frame 3 of the suturing instrument 26 and is detachably attached to a thread axle 28 having a spring 27. The thread supply 24 has a flange 24a which is formed with a plurality of cutouts 24b on its circumference. The flange 24a is partially exposed out of one of the covers of the suturing instrument 26, i.e., in the instant embodiment, via a cutout 29a of the cover 29.

The numeral 30 is a braking mechanism which is composed of a braking shaft 31 planted on the machine frame 3, a braking body 32 which is pivoted on the braking shaft 31 and is formed with an operating portion 32a at one end and with an engaging portion 32b at the other end, and a braking spring 33 which biases the braking body 32 around the braking shaft 31 in the clockwise direction in FIG. 1, and engages the engaging portion 32b into the respective cutout 24b of the thread supply 24. The operating portion 32a of the braking body 32 is exposed out of one of the covers of the suturing instrument 26, i.e., in the instant embodiment via cutouts 34a and 34b of cover 34. The thread supply 24 is moderately rotated out of the suturing instrument 26 via the flange 24a by engagement between the engaging portion 32b and the cutout 24b of the flange 24a, but the biasing force of the braking spring 33 is such that the thread supply 24 is not rotated against the force acting via the suturing thread 25 at tightening the thread as will be later mentioned.

The numeral 35 is a thread tension composed of a shaft 36 which is formed with a female screw 36a at its top portion, a tubular portion 36b, and a male screw 36c at its lower portion, and whose lower end is fixedly screwed into the machine frame 3 with a nut 37, and, in the order from the lower part, a spring 38, an adjusting dial 39, a spring 40, a thread tension disc 41 and a thread tension screw 42 secured on the top of the shaft 36. The adjusting dial 39 is partially exposed via the cutout 29b of the cover 29 and the cutout 34c of the cover 34. The thread tension disc 41 is defined with a couple of bendings 41a and 41b into which a tongue 43a of the thread tension disc 43 is moderately engaged to determine direction of the thread tension disc 41.

The suturing thread 25 passes, as shown in FIG. 1, inside of the bending 41a, turns around the tubular portion 36b and is drawn out along the inside of the bending 41b, during which it is supported between the thread tension disc 43 and the thread tension disc 41 which is biased upwardly by the spring 40 and effected with tension. The thread tension is adjusted by rotating operation of the adjusting dial 39 outside of the suturing instrument.

A main body 44 of the suturing instrument is composed of the machine frame 3 and the needle bar supporter 16 attached thereto, and is provided with the cover 29 by the screws 45 and 46 and the cover 34 by the disc screws 47, 48 and 49.

A further reference will be made to actuation of the embodiment according to the invention. The sequence in operation of the embodiment comprises taking off the cover 29 from the main body 44, attaching the thread supply 24 coiling the suturing thread 25 on the thread axle 28 under the condition of pressing the operating portion 32a of the braker 32, drawing out the suturing thread 25 from the thread supply 24, passing the thread between the thread tension discs 41 and 43 of the thread tension mechanism 35, as shown in FIG. 1, and into the guide hole 18a of the thread guide piece 18 through the thread guide groove 16a and advancing along the oblong groove 20b of the curved needle 20 into the needle hole 20a, drawing out the thread 25 from the needle eye as much as for the part to be sutured up, and combining an end of the thread and the thread hole 13h of the shuttle 13 held between the shuttle holder element 10 and the shuttle claw 12 to make a suturing thread 51 at the shuttle side (called as "shuttle thread" hereafter).

Prior to penetration of the curved needle 20 into the part to be sutured, the shuttle is drawn toward the main body 44 together with the shuttle thread 51 to avoid hindering the penetration of the curved needle.

When the curved needle 20 is penetrated into the parts 52 and 53 to be sutured from a penetrating hole 52a, the needle thread 54a pulled in straight (as shown in FIG. 6) between the needle eye 20a and the penetrating hole 53a, is changed into a loop of crescent 54L of the needle thread together with the needle thread 54b guided in the oblong groove 20b. The shuttle 13 connected with the shuttle thread 51 is moved to a remote side from the main body 44 and is advanced into the needle thread loop 54L to catch this loop, and then if the shuttle 13 is returned to the main body 44, the shuttle 13 makes a round thread 51, and the shuttle thread 51 crosses with the needle thread 54 as shown in FIG. 8. The curved needle 20 is pulled out from the penetrating hole 52a, and the needle thread 54 and the shuttle thread 51 are tightened to form an initial stitch of lock stitch.

The penetration point is moved so that the curved needle 20 is caused to pass into the parts 52 and 53 to be sutured, and a needle thread loop 54L is formed as shown in FIG. 10. The shuttle 13 is reciprocated to cross, as shown in FIG. 11, the needle thread 54 and the shuttle thread 51, and the curved needle 20 is drawn out from the penetration hole 52a as shown in FIG. 12. The needle thread 54 and the shuttle thread 51 are tightened to form a stitch next to the lock stitch. The above mentioned operation is repeated and finally the needle thread 54 and the shuttle thread 51 are combined to form continuously suturing formation as shown in FIG. 13.

In the above mentioned suturing operation, and with reference to FIG. 14, an explanation will be made to a process that the shuttle 13 goes into the needle thread loop 54L and goes round a needle thread portion 54a so as to cross the needle thread loop 54L and the shuttle thread 51. When the shuttle holder 8 is moved apart from the main body 44, the front portion 13b of the shuttle 13 goes under the needle thread portion 54a as shown in FIG. 14 and catches the needle thread loop 54L. The shuttle 13 is effected with force from the needle thread portion 54a under the condition that the front portion 13b is guided into the guide groove 10b of the shuttle holder element 10, and the front portion 13b is tilted downwardly. By the subsequent movement of the shuttle 13, the needle thread portion 54a is passed, as shown in FIG. 15, between the slope 13e of the front portion 13b and the hook 12a of the shuttle claw 12, and is passed between the upper surface of the main body 13a of the shuttle 13 and the shuttle claw 12 as being guided by the shuttle guide pieces 12c, and it reaches a condition shown in FIG. 16.

The condition shown in FIG. 16 is remotest from the main body 44. When the shuttle holder 8 is moved toward the main body 44, the needle thread portion 54a is passed between the bottom 13c of the main body 13a of the shuttle 13 and the shuttle holder element 10. In the second half of this passing, the shuttle 13 is so tilted by the needle thread portion passing that the front portion 13a is moved up. Under this condition, the front portion is guided into the guide groove 12b of the shuttle claw 12, and the shoulder 13j of the main body 13b is contacted to the inner face 12e (shown in FIG. 17) of the hook 12a. By the subsequent movement of the shuttle 13, the needle thread portion 54a is passed between the front portion 13b and the tongue guide piece 10a of the shuttle holder, element 10, and the shuttle thread 51 connected to the shuttle 13 goes round the needle thread portion 54a so as to cross the needle thread loop 54L and the shuttle thread 51 as shown in FIG. 18.

During crossing the needle thread loop 54L and the shuttle thread 51, the shuttle 13 is effected with the external force via the needle thread portion 54a of the needle thread loop 54L, and it is moved under the condition that it is held by the shuttle claw 12 and the shuttle holder element 10, and within the whole movable scope the front portion 13b is engaged with at least one of the guide grooves 10b or 12b, and the shuttle 13 may smoothly get out the thread without slipping out the shuttle holder 8.

As having discussed above, according to the invention, the suturing thread at the shuttle side and the suturing thread at the curved needle are crossed, and the shuttle having the thread is not slipped out from the shuttle holder during the suturing operation in the lock stitching practice, and the shuttle smoothly goes through the needle thread loop so as to exactly cross and knot the shuttle thread and the needle thread so that the stable stitchings are always formed.

It will be understood that each of the elements described above, or two or more together, may also find a useful application in other types of surgical suturing instruments differing from the types described above.

While the invention has been illustrated and described as embodied in a surgical suturing instrument, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. In a surgical suturing instrument having a curved needle carrying a suturing thread and mounted on a needle supporting means and a reciprocally movable shuttle holding means carrying a shuttle to which the suturing thread is connected to form a shuttle thread, the suturing thread being formed into a thread loop through which said shuttle is passed to form in cooperation with said needle, suturing stitches in two parts being sutured up, a combination comprising a shuttle having a said longitudinal center line and being symmetrical relative to said center line, said shuttle including a main body having an upper face and formed with a front end and a rear end, and a front end portion outwardly extending from said front end of the main body, said front end portion being formed with a thread passing hole and having a sharp end catching the thread loop, said front end portion having an upper sloped surface extending between said sharp end and said front end of the main body, and a lower sloped surface extending between said bottom surface and said front end of said main body; and said shuttle holding means including a shuttle holder and a shuttle claw secured to the shuttle holder so as to accommodate said shuttle therebetween, said shuttle holder being formed with a first guide groove engaging to engage and guiding said front end portion of said shuttle, said shuttle claw having a front part and a rear part, said front part having a second guide groove engaging guiding and guide said front end portion of the shuttle, said rear part of said shuttle claw being formed with a pair of opposite shuttle guide pieces which define an inner face of the shuttle claw, said guide pieces and said main body of the shuttle being so dimensioned that clearances are made between the upper face of said main body and the inner face of the shuttle claw, and between the rear end of said main body and said inner face to allow the suturing thread to pass through said clearances, said front end portion moving from said first guide groove to said second guide groove and vice versa, whereby the shuttle carrying the thread is prevented from being slipped out from said shuttle holding means during the suturing operation.

2. The combination of claim 1, wherein said main body has a height continuously decreasing from its front end to its rear end along said center line.

3. The combination of claim 2, wherein said main body has a width continuously decreasing from its front end to its rear end relative to said center line.

4. The combination of claim 3, wherein said main body at its front end is formed with two opposite round shoulders extending from said front end portion towards the rear end of the body.

5. A method of suturing parts in a surgical operation utilizing a suturing instrument having a curved needle whose curvature lies in a plane perpendicular to the longitudinal axis of said instrument, said curved needle having a hole and oblong guiding groove for carrying a thread, a reciprocally movable shuttle holding means having a holder with a guide groove and a claw with a guide groove both being cooperatively mounted to incorporate therebetween a shuttle having a main body with a sloping front end portion containing a thread hole, said shuttle having at least one expanded round shoulder and at least one correcting face, wherein the steps comprise:

(a) threadably moving said thread through said oblong groove and through said needle hole of said curved needle;

(b) fixedly attaching one end of said thread to said thread hole of said sloping front end portion of said shuttle so that a shuttle thread is formed;
(c) inserting said curved threaded needle through said parts to be sutured so that a thread loop is formed;
(d) moving said shuttle towards said thread loop so that said sloping front end portion is rockably movable between said guide groove of said shuttle holder and said guide groove of said shuttle claw so that said thread loop is cooperatively caught by said sloping front end portion of said shuttle, said sloping front end carrying said shuttle thread;
(e) crossing said shuttle thread with said needle thread by said rockably movable motion of said shuttle;
(f) removing said curved needle from said parts to be stitched and forming a stitch.

* * * * *